US006916968B2

United States Patent
Shapira et al.

(10) Patent No.: US 6,916,968 B2
(45) Date of Patent: Jul. 12, 2005

(54) URINE DETECTION SYSTEM AND METHOD

(75) Inventors: Shmuel Shapira, Sherwood, OR (US); Ron A. Tsur, Banks, OR (US)

(73) Assignee: Sysmore, Inc., Lake Oswego, OR (US)

( * ) Notice: Subject to any disclaimer, the term of this patent is extended or adjusted under 35 U.S.C. 154(b) by 328 days.

(21) Appl. No.: 10/253,807

(22) Filed: Sep. 23, 2002

(65) Prior Publication Data

US 2003/0060789 A1 Mar. 27, 2003

Related U.S. Application Data

(60) Provisional application No. 60/373,637, filed on Apr. 19, 2002, provisional application No. 60/357,624, filed on Feb. 20, 2002, provisional application No. 60/354,530, filed on Feb. 8, 2002, provisional application No. 60/348,381, filed on Jan. 16, 2002, provisional application No. 60/344,795, filed on Jan. 7, 2002, and provisional application No. 60/324,278, filed on Sep. 25, 2001.

(51) Int. Cl.[7] .................................................. A61F 13/15
(52) U.S. Cl. .................. 604/361; 604/362; 604/385.01; 340/573.5; 340/604; 340/571
(58) Field of Search ................................. 604/361, 362, 604/360, 385.01; 340/571–604

(56) References Cited

U.S. PATENT DOCUMENTS 3,759,246 A  *  9/1973  Flack et al. ................. 600/573
5,459,452 A       10/1995  DePonte
5,570,082 A       10/1996  Mahgerefteh et al.
5,760,694 A        6/1998  Nissim et al.
5,904,671 A  *    5/1999  Navot et al. ................. 604/361
6,091,336 A  *    7/2000  Zand et al. .................. 340/604
6,774,800 B2  *   8/2004  Friedman et al. ......... 340/573.5
2002/0070864 A1   6/2002  Jeutter et al.
2002/0070868 A1   6/2002  Jeutter et al.

FOREIGN PATENT DOCUMENTS

JP    2001289775 A    10/2001
JP    2001325865 A    11/2001
JP    2001338827 A    12/2001
JP    2002071584 A     3/2002

* cited by examiner

Primary Examiner—Jacqueline F. Stephens
(74) Attorney, Agent, or Firm—Kolisch Hartwell, P.C.

(57) ABSTRACT

A urine detection system and method. According to one aspect of the invention, the method includes generating a magnetic field within an effective distance of a potentially wetted area, and conducting a plurality of measurements to construct a magnetic energy distribution function corresponding to the potentially wetted area. The method further includes comparing at least one parameter of the magnetic energy distribution function to a set of stored parameters corresponding to known wetness conditions to identify a wetness condition of the potentially wetted area.

28 Claims, 3 Drawing Sheets

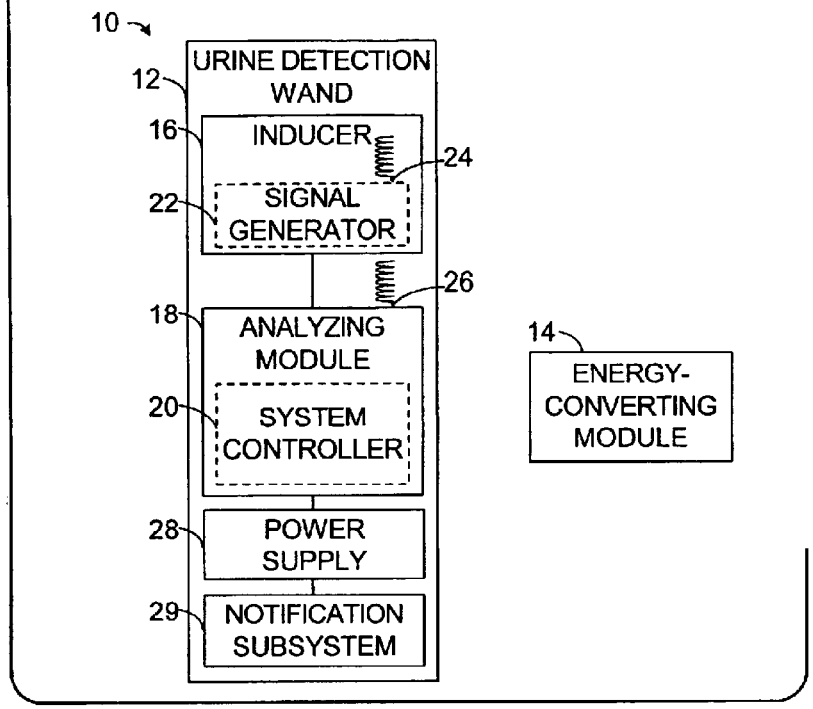
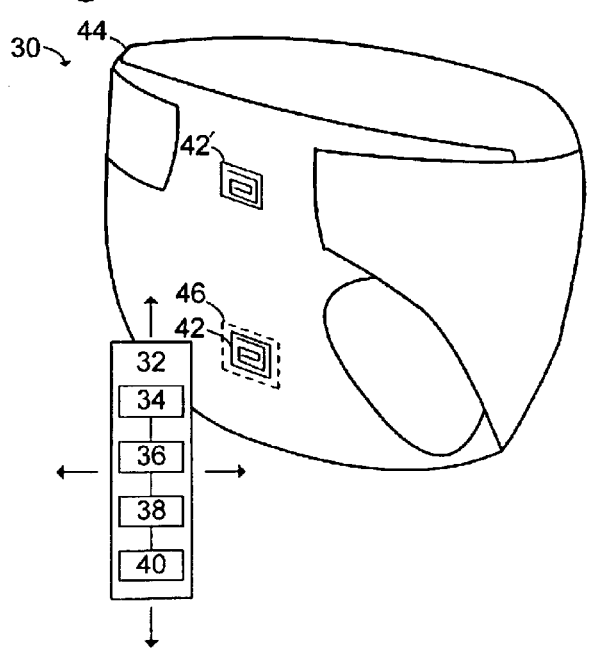
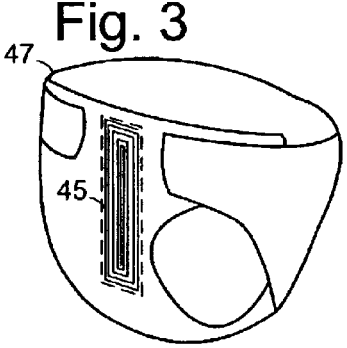

URINE DETECTION SYSTEM AND METHOD

CROSS-REFERENCE TO RELATED APPLICATIONS

This application claims priority under 35 U.S.C. § 119 from the following co-pending provisional patent applications, which are incorporated herein by this reference, in their entirety, and for all purposes: Wetness Detector and Messaging System, Ser. No. 60/324,278, filed Sep. 25, 2001; Monitoring and Messaging System, Ser. No. 60/344,795, filed Jan. 07, 2002; Monitoring and Messaging System, Ser. No. 60/348,381, filed Jan. 16, 2002; Monitoring and Messaging System, Ser. No. 60/354,530, filed Feb. 8, 2002; A System and a Method for Monitoring Fluid in Absorbent Articles, Ser. No. 60/357,624, filed Feb. 20, 2002; and Contact-less Monitoring and Messaging System, Ser. No. 60/373,637, filed Apr. 19, 2002.

BACKGROUND OF THE INVENTION

In the past, detecting the presence of urine, for instance in a diaper or bedding, has been accomplished by physically touching the potentially wetted area. For convenience, speed, sanitation, and similar reasons, this method is less than ideal, particularly in a managed care environment. In such environments, urine detection is an ongoing process. Several patients may need to be repeatedly tested, which can be a time consuming, physically demanding, undesirable task. Often times, patients are in beds, covered with blankets, and testing for urine in such circumstances is difficult using conventional methods. Some detection methods utilize visual indicators, but these methods require removal of clothing and/or blankets, and cannot discretely be used by an adult wearing a diaper in public.

To maximize the utility of urine collection articles, such as diapers, such articles must be changed when they have collected the proper amount of urine. Changing a urine collection garment too soon can be wasteful because the maximum effectiveness of the garment is not utilized. Changing a garment too late may cause the wearer discomfort and/or irritation, and may also allow urine to spread outside of the garment. Therefore, to maximize the effectiveness of such garments, it is desirable to be able to determine the relative amount of urine that has been collected by such a garment so that the garment may be changed at the proper time.

SUMMARY OF THE INVENTION

A urine detection system and method are provided. According to one aspect of the invention, the method includes generating a magnetic field within an effective distance of a potentially wetted area, and conducting a plurality of measurements to construct a magnetic energy distribution function corresponding to the potentially wetted area. The method further includes comparing at least one parameter of the magnetic energy distribution function to a set of stored parameters corresponding to known wetness conditions to identify a wetness condition of the potentially wetted area.

BRIEF DESCRIPTION OF THE DRAWINGS

FIG. 1 is a schematic view of a urine detection system according to an embodiment of the present invention.

FIG. 2 is a schematic view of an exemplary urine detection wand collaborating with a corresponding exemplary energy-converting module in accordance with an embodiment of the present invention.

FIG. 3 is a schematic view of a urine collection article configured for use with the urine detection wand of FIG. 2.

DETAILED DESCRIPTION OF THE INVENTION

Figure 4:
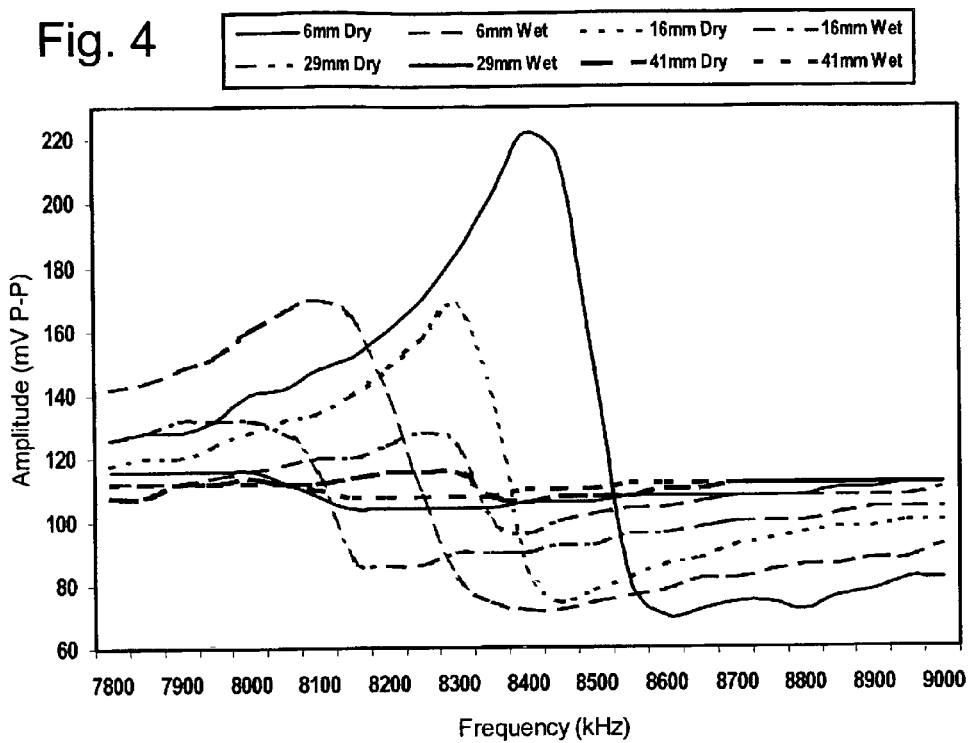
FIG. 4 is a graph of response curves generated from measurements taken with a urine detection system in accordance with an embodiment of the present invention.

A urine detection system in accordance with some embodiments of the present invention is schematically illustrated at 10 of FIG. 1. As described in detail below, the urine detection system may be used to detect urine excretions, such as in a diaper, clothing, bedding, etc. Easy and accurate detection of urine excretions may be particularly useful in a managed care environment, although the present invention may be used to detect urine, or other ionized substances, in virtually any environment for virtually any purpose. For example, embodiments of the present invention may be used to detect excretions of an infant or those occurring when an individual is being trained to use a toilet and/or stop bedwetting, as well as when an individual suffers from urinary incontinence. Some embodiments of the present invention permit urine detection measurements to be performed through clothing and/or bedding, and each measurement may be performed in a matter of seconds without having to unnecessarily move the tested individual. Furthermore, it is within the scope of the invention to test not only the presence of urine, but also the amount of urine present. As described below, the urine detection system may include one or more dedicated devices configured to detect the presence of urine. In some embodiments, componentry of the system may be distributed between one or more devices that may also be configured to provide functionality other than urine detection functionality.

Urine detection system 10 includes a detection wand 12 and at least one energy-converting module 14. As shown, the detection wand may include an inducer 16 and an analyzing module 18. The inducer may be designed to introduce a magnetic field into a test environment, such as a diaper. In some embodiments, the inducer may include a signal generator 22, such as a radio frequency oscillator, operatively coupled to an exciter coil 24 so that the signal generator may drive an electrical signal in either transient or continuous form through the exciter coil to produce the desired magnetic field. The signal generator may include a voltage-controlled oscillator, phase-lock-loop based synthesizer, direct digital synthesizer, etc. The signal generator may be configured to selectively adjust the waveform, frequency, or duty cycle of the driven signal to produce the desired magnetic field. As described herein, the driven signal may be adjusted, for example by a system controller 20.

Changing current in the inducer may vary the magnetic flux through the energy-converting module, and thus, may induce an electromotive, mechanical, or other force in the energy-converting module. Therefore, the inducer and the energy-converting module may engage in mutual inductance with one another, as well as other participating elements, such as other energy-converting modules. The energy distribution between the energy-converting module and the inducer may be measurably influenced when the urine detection system is within an effective distance from a volume of urine. Therefore, measurement and analysis of the energy distribution may be used to detect urine. The effective distance may vary considerably depending on the configuration of the urine detection system. In some embodiments, an energy-converting module may be physically separated from the urine detection wand, and in some embodiments, the energy-converting module may be incorporated into the urine detection wand, as a sampling coil, for example.

The energy-converting module may utilize a conductive loop (coil) to convert magnetic energy into electrical energy. Such a coil may be utilized in various embodiments of the present invention via at least two methods. Using one method, the coil may be employed to directly measure energy distribution. In such a configuration, herein referred to as a sampling or reference coil, the coil may be fixed relative to the inducer, and the induced voltage in the coil may be measured across the coil. Using the other method, the coil may collaborate with the inducer to facilitate detection of urine, although measurements are taken apart from the coil itself. Such a coil, herein referred to as a collaborating coil, may be movable relative to the inducer, and is typically configured as a part of a resonance circuit. In either case, such energy-converting modules may include one or more components that collectively constitute the sampling coil or collaborating coil. Furthermore, it should be understood that sampling coils and collaborating coils may be variously configured depending on the particular configuration of a particular urine detection system.

In some embodiments, the energy-converting module includes a collaborating coil configured as a part of an inductive/capacitive resonating circuit, as is described in detail below with reference to FIG. 2. With such an energy-converting module, mutual oscillation between the inducer and the energy-converting module may occur if the distance between the inducer and the energy-converting module is within an operating range, and the frequency of the generated alternating magnetic field corresponds to the resonant frequency of the energy-converting module. The mutual oscillation typically is characterized by a measurable increase in the amount of energy being exchanged between the inducer and the energy-converting module, which is reflected in the energy distribution between the inducer and the energy-converting module. As described below, ionized substances, such as urine, may affect the energy distribution. It should be understood that it is also within the scope of the invention to implement other non-electrical resonators, such as mechanical resonators including a magneto elastic resonator. Two or more resonators configured to differently affect the energy distribution of the system in the presence of a quantity of ionized substance may be utilized to provide comparative information or to validate results.

In some embodiments, the energy-converting module may include a sampling coil, as is described in detail below with reference to FIG. 6. In such embodiments, the induced signal at the sampling coil may be measured across the coil itself. Furthermore, it is within the scope of the invention to include an optional reference coil, from which a reference signal may be measured. The sampling coil may be configured to respond to a particular magnetic field in the same way as the reference coil so that discrepancies detected between the sensing and reference coils may be attributed to external factors. For example, a sampling coil and a reference coil may be fixed at substantially equal distances and in similar orientations relative the inducer. In an isolated environment, the inducer typically will induce equal (or nearly equal) electromotive forces in the sampling coil and the reference coil if the coils are similarly configured. Therefore, the effects of outside influences, such as urine, which may depend on position relative to the coils, may be measured and analyzed. In some embodiments, the sampling coils may not be similarly configured and/or similarly spaced relative the inducer. However, it should be appreciated that in such configurations, differential measurements are still possible.

Analyzing module 18 may be configured to measure energy distribution between the inducer and one or more energy-converting modules. The analyzing module may include a sampling coil 26 for taking such measurements. Exciter coil 24 of the inducer may alternatively or additionally be used to take such measurements. It is within the scope of the invention to utilize more than one sampling coil in order to facilitate differential signal measurements. The analyzing module is typically integrated into the urine detection wand, although it is within the scope of the invention to externally house the analyzing module, or portions thereof. Data acquisition componentry of the analyzing module may also be configured to receive measurements from other sources. Analyzing module 18 typically includes an analog-to-digital converter for converting analog signals into digital information. The digital information may be analyzed and/or stored. In particular, the analyzing module may store digital information constituting a constructed energy distribution function that models the measured energy distribution pattern. The analyzing module may include system memory for storing a set of parameters corresponding to known wetness conditions, as well as other conditions such as magnetic coupling coefficients, as described below. A processor of the analyzing module may execute instructions that evaluate the magnetic energy distribution function, such as by comparing parameters of the function to the set of stored parameters corresponding to known conditions. In this manner, the measured energy distribution pattern may be linked to a wetness condition corresponding to a pre-determined energy distribution pattern, as represented by the stored parameters in system memory.

The analyzing module may include a system controller 20 for performing a variety of supervisory functions including data acquisition and storage, decision-making, scheduling, coordination, and execution of the other various system functions discussed herein. For example, the controller may be configured to set the signal driven through the inducer, analyze received data, compare received data with data derived from known wetness conditions, adjust the driven signal based on the analyzed data, etc. The system controller may initiate an automatic detection mode in which data acquisition cycles are executed according to preset time intervals, or the system controller may defer scheduling to a tester or a separate system. The system controller may include a processor, such as an embedded hardware microcontroller, which may include, or interface with, data storage devices and/or peripheral devices, such as timers, counters, I/O ports, etc. In addition, the wand may also include a power supply 28 and a notification subsystem 29.

The urine detection wand may be configured in a variety of shapes and/or sizes. In particular, the wand may be sized and weighted for easy manual manipulation by a tester. For example, a hand-held wand may be used to reach around a bedded patient without having to move the patient. The relatively small size of the wand also may permit the wand to be easily carried from one test area to the next, for example, to test several patients located in several different rooms. It is also within the scope of the invention to incorporate the urine detection wand, or parts of it, into another device, such as a personal data assistant, watch, cellular phone, glove, belt, etc. The system may communicate with other systems through a communication interface, such as a wired or wireless communication interface. The required proximity of the urine detection wand relative to the potentially wetted area may vary depending on the particular configuration being used.

As is described with reference to the following illustrative examples, the urine detection system may be variously configured. In some embodiments, energy-converting modules of the urine detection system may include a sampling coil, while others may include a collaborating coil, such as a resonator. Some systems may utilize both collaborating coils and sampling coils. Furthermore, an energy-converting module of a particular urine detection system may be spatially fixed relative to the inducer, or may be freely movable relative to the inducer. It is also within the scope of the invention to use a combination of fixed and movable energy-converting modules. Similarly, exposed energy-converting modules and energy-converting modules insulated from contact with an ionized substance, such as urine, may be variously implemented. Some energy-converting modules may include additional circuitry for modifying the transferred energy to include identifiable characteristics, such as modulation. Such a configuration may be employed to facilitate differentiation between closely located modules. Furthermore, some energy-converting modules may include a data storage mechanism for storing data, such as an identifier that may be presented to an analyzing module to facilitate identification of a particular energy-converting module. This may be useful, for example, if a common analyzing module is used in conjunction with more than one energy-converting module. It should be understood that many combinations are possible, and the following are provided as non-limiting illustrative examples.

FIG. 2 shows a urine detection system 30 that includes a detection wand 32 with an inducer 34 and analyzing module 36. The wand also may include a power supply 38 and a notification subsystem 40. As shown, an energy-converting module 42 in the form of a collaborating coil is separated from and movable relative to the urine detection wand. The energy-converting module includes an inductive/capacitive resonating circuit in a planar configuration. Such a resonator may be very small. In the illustrated embodiment, the resonator is shown to be approximately the size of a postage stamp (1 inch×1 inch×0.02 inch), although larger or smaller resonators are within the scope of the invention. The resonator may be passive, and therefore not require a dedicated power source. The resonator's small size, and its ability to operate without a dedicated power source, allow the resonator to be used in a variety of different applications. For example, the resonator may be configured as a tag or decal that may be selectively attached to a urine collection article 44, as is illustrated in FIG. 2. Such a configuration allows for aftermarket modification of any urine collection article. Urine collection articles may include absorbent garments, diapers, absorbing pads, under garments, bed coverings, urine bags, and other types of garments and sanitary products. As is discussed below, the energy-converting module may be secured to the outer-surface of a diaper, and need not come in direct contact with urine. The resonator may also be integrated into a urine collection article (insulated or non-insulated). In either case, the close association with a potentially wetted area may increase detection accuracy in some applications.

More than one energy-converting module may be included in the urine detection system. For example, FIG. 2 shows a second resonator 42', which has natural resonance frequency different than the natural resonance frequency of resonator 42, is attached to another area of urine collection article 44. Plural energy-converting modules allow different areas of a urine collection article to be tested, so that the relative wetness of the various areas may be determined. This may be useful in determining if a urine collection article is ready for changing, for example by recognizing the differential wetness characteristics of different regions of a garment to determine the difference from a lightly wetted garment and a garment that should be changed. Furthermore, two or more coils may be connected to one another and at least one capacitor to constitute a single electrical resonator that may enter a state of resonance when at least one of the coils is within the magnetic field of the inducer. In this manner, plural energy-converting modules may be networked together, so that participation of one energy-converting module may yield information relating to the wetness of an area associated with both itself and another energy-converting module. In other embodiments, a single elongated collaborating coil 45 may be used in conjunction with a urine collection article 47, as shown in FIG. 3. Such an elongated collaborating coil may be positioned so that as the urine collection article becomes increasingly saturated, a greater percentage of the collaborating coil will be within an effective range from the urine. Therefore, the relative amount of urine collected may be identified.

The energy-converting modules may be insulated from urine by positioning the module outside of a protective shell of an absorbent article and/or via a moisture shell 46. As used herein, "insulated from moisture, excretion, and/or urine" describes an energy-converting module with functional components physically protected from urine. The moisture shell and/or other non-functional components may come into contact with urine. Similarly, the urine may affect the energy-converting module, such as via magnetic fields. The moisture shell may be a waterproof envelope or other suitable structure or coating for preventing urine from contacting the circuitry of the module. The moisture shell may be useful in preventing urine from directly interacting with metals or other materials that may be used to construct the energy-converting module, thereby limiting potential harm to a body exposed to the urine. The moisture shell may also prevent urine from shorting an electrical circuit included in an energy-converting module.

Of course, in some embodiments, an energy-converting module without a moisture shell may be used. Such an energy-converting module, which may include an electrical resonator, may be configured to lose its ability to attain mutual oscillation when in the presence of urine, because it is short circuited, for example. Therefore, the non-insulated energy-converting module may serve as an indication of the presence of urine, even for small quantities of urine. An energy-converting module insulated from moisture may be used in combination with a non-insulated module to facilitate quantity-related detection. Furthermore, the insulated energy-converting module may be used to determine that a non-insulated energy-converting module is not participating as a result of a condition other than contact with urine.

In application, detection wand 32 may be used to collaborate with one or more energy-converting modules, such as module 42 and/or module 42'. As described above, inducer 34 may generate an alternating magnetic field, which may be at least partially absorbed by the energy-converting modules. The analyzing module may then track changes in the energy distribution between system components. In general, the energy that is exchanged between the inducer and an energy-converting module(s) depends on the magnetic coupling coefficient, their relative impedance, and the frequency of the magnetic field. An ionized substance may affect the impedance of a system component, such as by changing parasitic capacitance or magnetic permeability, and/or change the properties of the magnetic field such as by absorption or distortion.

Mapping the behavior of the system during a data acquisition cycle yields one or more response curves, and/or magnetic energy distribution functions, representing the energy distribution pattern, as described below with reference to FIGS. 4 and 5. A response curve may represent time-correlated variations in signal amplitude to different frequencies of an alternating magnetic field as measured at different locations within the system. Similarly, a response curve may represent variation of signal level in time, correlated with the build up and collapse of a magnetic field associated with an electrical pulse.

In the present implementation, the detection system is designed so that the energy distribution reacts to an ionized substance located at an effective distance within the shared magnetic field, and yields a system response curve and/or magnetic energy distribution function that is distinctly different from when the system is inert. Therefore, analysis of the response curve and/or magnetic energy distribution function may be used to detect the presence of urine, which is an ionized substance. If the system is allowed to enter into a state of sympathetic oscillation, the response curve may exhibit a unique behavior associated with a hysteretic effect. Identifying this hysteretic effect may provide an additional method of distinctly characterizing system response, which is not solely dependent on amplitude measurements, and may potentially improve the system's signal to noise ratio.

The orientation and/or distance between the inducer and an energy-converting module may affect the value of the magnetic coupling coefficient (K). Therefore, accurate urine detection may depend on properly identifying the magnetic coupling coefficient. FIG. 4 shows eight curves corresponding to wet and dry measurements respectively taken at distances of 6 mm, 16 mm, 29 mm, and 41 mm. The distance between an energy-converting module and the inducer directly affects the K value. As shown, different Ks typically result in different response curves for respective dry and wet conditions. A response curve associated with a specific K may also be found in an intermediate position between a curve representing a dry condition and a curve representing a fully wet condition. It is also within the scope of the invention to process curves that represent a partially wetted condition.

Parameters from a plurality of known energy distribution patterns may be stored in system memory and used to identify a coupling coefficient during a urine detection procedure. For example, parameters from a magnetic energy distribution function that models a measured energy distribution pattern may be compared to stored parameters, which act as a reference. In this manner, the measured energy distribution pattern may be linked to a known energy distribution pattern, and the coupling coefficient associated with the known energy distribution pattern may be extrapolated to the measured energy distribution pattern. Two or more energy-converting modules, each configured to respond differently to the same magnetic field, such as by having a different resonance frequency and resistance, may be employed to provide comparative information and assist in calculating K.

Identification of the relevant K value typically greatly improves detection accuracy and helps properly translate observed energy levels into useful information regarding the presence or quantity of urine in the tested region. The system may compensate for changing K values by using mathematical modeling of expected signal behavior for specific discrete values of K. Techniques such as curve fitting and interpolation facilitate the numerical approximation of a curve to be performed using only a limited number of control parameters. Movement between the inducer and energy-converting modules during a data acquisition cycle may be compensated for by adaptive monitoring strategies. Differences between the response curves of two or more consecutive measurements may indicate the occurrence of movement. Changes in system response that can be attributed to movement may than be calculated and compensated for.

A data acquisition cycle may involve a frequency sweep within a predetermined range while concurrently sampling (measuring) a signal representing the level of energy in a chosen region in the system. As discussed above, signal sampling may include digital to analog conversion of measured signals, whereby the measured signals are successively sampled at fixed intervals to produce a series (set) of discrete measurement values that, in turn, may be stored in system memory, either individually, as a set of values, or as a set of parameters defining a constructed magnetic energy distribution function. The signal-sampling rate may be synchronized with the rate the inducer changes the frequency of the generated magnetic field (sweep rate). This helps ensure that each discrete measurement is closely associated with a known frequency, or frequency sub-range. Using this cycle, an array of numerical values representing the instantaneous energy for each frequency (sub-range) may be acquired and selectively stored in memory for further analysis. For example, using the array, the acquired signal frequency-amplitude response curve may be studied for characteristic patterns that indicate various wetness conditions associated with different Ks. Depending on the application, the frequency sweep method may be either ascending (low frequency to high frequency), descending (high frequency to low frequency), or virtually any combination of ascending and descending sweeps. Furthermore, the frequency range for each sweep may be strategically focused about a particular active range to improve detection accuracy.

In addition to controlling the range of the frequency sweep, the rate at which the frequencies are swept may also be strategically adjusted. Similarly, the sensitivity of signal detection may be adaptively adjusted to compensate for weak signals or reduce noise detection. The system may be equipped with a gain control device for adjusting the dynamic range of the amplitude of the driven signal. When the system is activated, the gain control settings are typically configured to a default value. The default value may provide a balance between low gain, where small changes in signal level may be difficult to detect, and high gain, where noise may be introduced. The system may maintain a circular histogram, containing the weighted averages for the most recent signal acquisition cycles, which may be used to adaptively adjust the setting of the gain control to an optimal position. Frequency range, sweep pattern, sweep rate, sensitivity, and other acquisition and analysis procedures may be strategically adapted alone or in combination.

The data analysis process typically involves extracting significant details from the data gathered during the most recent acquisition cycle (or a collection of the most recent cycles), calculating the system response curve/function, and interpreting the response curve/function. Selective regions of the curve may be identified as indicating significant events, such as a wetness condition. Data may be evaluated according to stored parameters representing pre-measured test curves that correspond to different combinations of Ks, urine quantities, and/or other variables (known conditions). Such evaluations may be useful in identifying the measured response curve. For example, a response curve may be matched to a particular test curve because the curves have substantially similar parameters. The conditions of the known test curve, such as relative wetness, coupling coefficient, etc., may be used to extrapolate the conditions of the potentially wetted area, and such conditions may be reported to a tester via the notification subsystem, which may include a display, audio speaker, data transmission interface or other suitable notification and/or communication mechanism.

The analyzing module may be designed to recognize measurements that are less than optimal due to the orientation or position of the urine detection wand. Furthermore, the analyzing module may be configured to alert an operator, such as via notification subsystem 40, that the disposition of the urine detection wand should be reorientated to achieve optimal measurements. The notification subsystem may also be configured to alert a tester to other conditions, such as a low battery condition, an error condition, etc.

Figure 5:
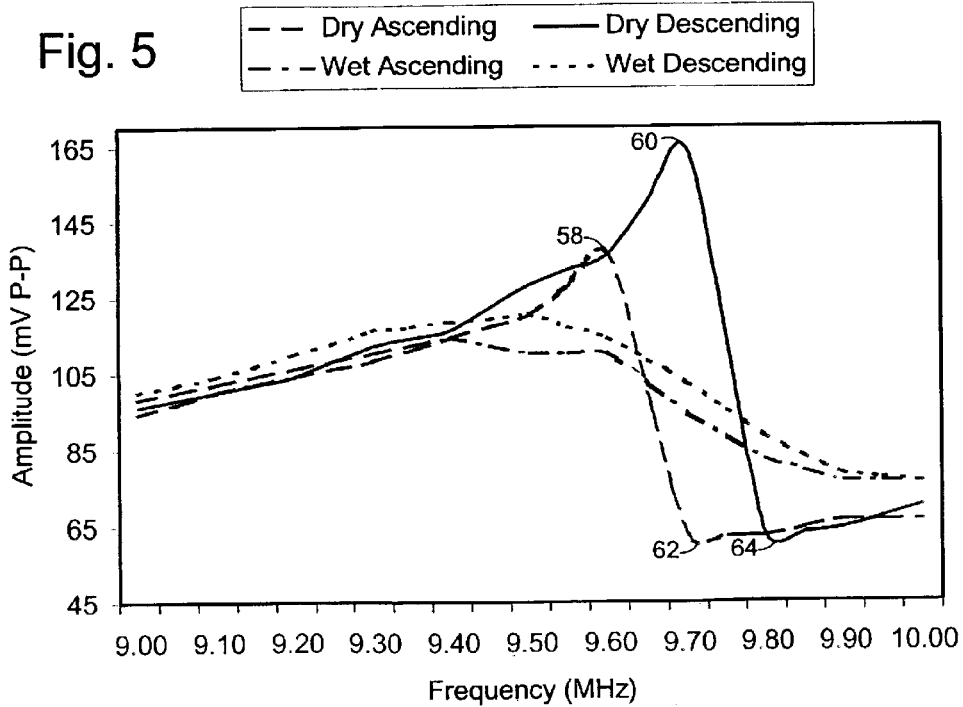
FIG. 5 is another graph of response curves generated from measurements taken with a urine detection system in accordance with an embodiment of the present invention.

FIG. 5 graphically illustrates measured response curves corresponding to ascending and descending frequency sweeps for exemplary wet and dry conditions. The depicted response curves represent a configuration having a collaborative coil attached to the external side of a protective shell of an absorbent pad, and measurements where taken across a sampling coil positioned 25 mm away from the exciting coil. Response curves 50 and 52 respectively represent ascending and descending frequency sweeps during a dry condition, while response curves 54 and 56 respectively represent ascending and descending frequency sweeps during a wet condition. For the purpose of simplicity, only a single ascending and descending sweep is shown for the respective wet and dry conditions. However, in practice, several ascending and/or descending frequency sweeps may be performed each second; and each sweep may be dynamically adjusted based on the current monitoring strategy. The results from each sweep may be considered individually and/or the results of several sweeps may be considered together, such as in a weighted average. Also, for the purpose of simplicity, each of the illustrated response curves corresponds to a measurement that was taken with the urine detection wand in the same orientation and position relative to the energy-converting module. The direction of the sweep, and the presence of urine are the only altered variables. Of course, in practice, the detection wand may move relative to the energy-converting module, and such movement may be reflected in the measured response curves. However, it is within the scope of the invention to limit potentially negative effects of such movement via software filters and/or adaptive monitoring strategies. For example, software may be executed to link an array of measured signals represented by a response curve or magnetic energy distribution function to known response curves associated with known K values and wetness conditions.

As is shown, the response curves span between 9.00 MHz and 10.00 MHz, the range of the frequency sweep used to measure the response curves in the illustrated example. Of course, other frequency ranges may be used. The four response curves generally track each other between 9.00 MHz and 9.40 MHz. Because this portion of the curves is not as dependent on relative wetness, it may be useful in determining the K value when the relative wetness is not known. Between 9.40 MHz and 10.00 MHz, it can be seen that the response curves do not track each other. This range provides useful information regarding the wetness condition of the measured environment. However, it should be understood that useful information may be extracted from other ranges, depending on the frequency the energy-converting module is tuned or similar factors.

Comparing dry curves 50 and 52 to wet curves 54 and 56, it may be appreciated that while the wet curves generally slowly increase in amplitude from 9.40 MHz to 9.50 MHz and then gradually decrease while moving to 10.00 MHz, the dry curves demonstrate an exaggerated increase in amplitude above 9.40 MHz and then an exaggerated decrease in amplitude before gradually moving towards the wet curves at 10.00 MHz. The dry curves respectively have maximum amplitude inflection points 58 and 60 and minimum amplitude inflection points 62 and 64 that help differentiate the wet curves from the dry curves. The wet curves also have maximum and minimum inflection points, however, the following discussion will focus on the dry curves for the purpose of simplicity.

The variation in signal amplitude, as shown between the maximum and minimum inflection points and nearby frequency ranges, can be used to determine the response curve associated with the energy transfer pattern exhibited by the system. Characterization of the curve may involve any of the following parameters: rate of change, span between inflection points, maximum and minimum, trend, repetition, and other parameters derived from numerical and statistical analysis methods such as Fourier Analysis. It should be understood, however, that other parameters may also be used. Furthermore, such parameters may be used to individually characterize each measured curve, and the parameters may be stored and/or used to compare measured curves to known curves. The parameters may define a magnetic energy distribution function that may be used in system testing.

The analyzing module may analyze measured curves in order to identify similarities and/or differences with respect to known curves associated with known Ks and wetness conditions. Such analysis may include comparisons between significant features of the respective curves, as may be characterized by one or more relevant parameters. In addition to curve parameters, the conditions present during the measuring of the known curves may be stored in memory, and used to determine the conditions present during a urine detection measurement. An example comparison may include comparing at least one parameter derived from measured behavior with a corresponding known parameter from a known response curve and determining if the derived parameter is within a predetermined range relative to the corresponding parameter from the known response curve. Such a comparison may be repeated for a series of parameters. If the comparisons link the measured behavior to a known behavior, according to pre-determined tolerance criteria, the conditions associated with the known behavior (relative wetness, wand disposition, etc.) may be extrapolated to the measured environment. In this way, curve comparisons may be used to identify the state of the measured system's behavior by relating known information about pre-measured behavior, such as wand disposition and relative wetness, to the measured behavior. The results of such comparisons may be used to convey information regarding the content of a urine collection article, such as a diaper, via a notification subsystem. An energy-converting module may modify the transferred energy to include identifiable characteristics. The analyzing module may extract such data, embedded in the response curve, and use it in the analysis process or forward the information for external analysis.

Identification of a hysteretic effect may provide useful information regarding the state of the system. For example, maximum inflection point 58 for the ascending dry curve occurs at a lower frequency than maximum inflection point 60 for the descending dry curve, although the respective sweeps were generated in a common environment. Similarly, minimum inflection point 62 for the ascending dry curve occurs at a lower frequency than minimum inflection point 64 for the descending dry curve. As shown, the frequency-amplitude response curve exhibits a unique nonlinear behavior associated with a hysteretic effect. Characterizing this hysteretic effect provides a method of distinctly characterizing system response, which is not solely dependent on amplitude measurements while improving the measurement system's signal to noise ratio.

As discussed herein, the system may adapt a monitoring strategy to better interpret curve behavior. For example, with respect to the measurements shown in FIG. 5, after recognizing that the curves approximately track one another between 9.00 MHz and 9.40 MHz, subsequent sweeps may be focused between 9.40 MHz and 10.0 MHz, which may allow for improved resolution and potentially increased accuracy. Similarly, gain may be increased or decreased to adjust the sensitivity of the measurement, and or the rate of sweep may be increased or decreased. It should be understood that such modifications may be made in real-time, dynamically responding to previous measurements. With every sweep, the monitoring strategy may use measured information to alter one or more subsequent sweeps. Furthermore, recursive sweeps may be performed throughout a testing cycle to verify results of previous sweeps.

Figure 6:
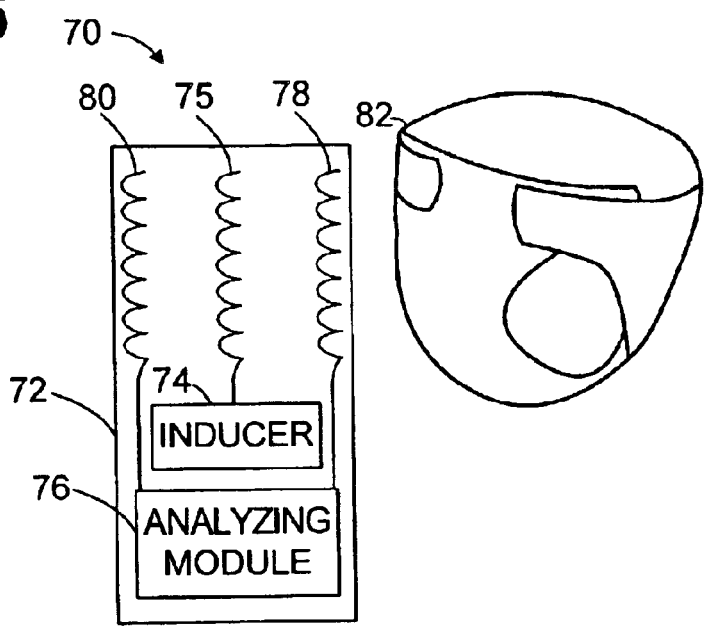
FIG. 6 is a schematic view of a urine detection system in accordance with another embodiment of the present invention.

FIG. 6 schematically shows a urine detection system 70, which includes a urine detection wand 72 including an inducer 74 with an associated exciter coil 75. The wand further includes an analyzing module 76, and a pair of energy-converting modules that respectively include sampling coil 78 and reference coil 80. As shown, the sampling coil and the reference coil are fixed on opposite sides of the inducer's exciter coil at substantially equal distances from the exciter coil. One or more signal samples may be taken at each coil, and used to construct respective magnetic energy distribution functions. Furthermore, a difference between the signals measured at each coil may be calculated, and may be used to calculate a difference function. For example, an array of sampled differences may be used to plot a curve, which may be matched to a known curve associated with known conditions. However, in some embodiments, a difference of a predetermined magnitude between the respective signals is sufficient to identify a wetness condition. Urine detection system 70 may, but is not required to, include one or more energy-converting modules separated from the urine detection wand. Such energy-converting modules may be used by urine detection system 70, as described above with reference to urine detection system 30. The effective detecting range of a urine detection system employing one or more sampling coils may be approximately 10 mm, although it is within the scope of the invention to configure systems with greater or lesser effective ranges. A range of about 10 mm provides the ability to detect urine through clothing. With the collaboration of a separated energy-converting module, the same wand may be used to detect urine from even greater distances and trough thicker layers such as blankets.

In application, detection wand 72 may be used to inspect a potentially wetted area, such as diaper 82. The sampling coil may be positioned near the potentially wetted area with the reference coil thereby being distally positioned. The inducer may produce a continuous sine wave, a rectangular waveform in either single pulse or pulse train, or similar signal. Such signals may induce corresponding signals at the sensing and reference coils, and the signal at the sampling coil may be compared to the signal at the reference coil. Urine's effect on the signal at either coil is typically at least partially dependant on that coil's distance from the urine, therefore the relative measurement may be useful for determining if the potentially wetted area is in fact wetted. In a dry condition, neither coil should be affected by urine, and the signal at both coils should be similar to one another. However, if urine is present, it will affect the coils differently, because it is closer to the sampling coil than the reference coil. The analyzing module may identify such a difference as being caused by a wet condition. Furthermore, the analyzing module may examine the character of each array of signal samples, such as by comparing the characteristics of an array of samples to characteristics of pre-measured signal arrays associated with known conditions, to detect the presence and/or quantity of urine. The above-described configuration permits the system to use relatively high gain settings to distinguish relatively small changes in the common magnetic field by overcoming common environmental factors including noise, temperature changes, etc. Furthermore, the configuration allows the wand to test virtually any potentially wetted area, and is not restricted to areas at which an energy-converting module has been placed.

While embodiments of the present invention have been particularly shown and described, those skilled in the art will understand that many variations may be made therein without departing from the spirit and scope as defined in the following claims. The description should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A method of detecting urine, comprising:
   generating a magnetic field within an effective distance of a potentially wetted area;
   conducting a plurality of measurements to construct a magnetic energy distribution function corresponding to the potentially wetted area; and
   comparing at lea at one parameter of the magnetic energy distribution function to a set of stored parameters corresponding to known wetness conditions to identify a wetness condition of the potentially wetted area, wherein the plurality of measurements are correlated in time to the build up and collapse of the magnetic field.

2. The method of claim 1, wherein generating a magnetic field includes driving a signal through an exciter coil.

3. The method of claim 1, wherein the plurality of measurements are correlated in time to different frequencies of the magnetic field.

4. A urine detection system, comprising:
   an inducer configured to generate a magnetic field within an effective distance of a potentially wetted area;

an energy-converting module configured to conditionally engage in mutual induction with the inducer; and an analyzing module configured to construct a magnetic energy distribution function that models an energy distribution pattern between the inducer and the energy-converting module, wherein the analyzing module is further configured to apply the magnetic energy distribution function to a set of stored parameters corresponding to known wetness conditions to identify a wetness condition of the potentially wetted area;

wherein the analyzing module compares parameters of the energy distribution function with the stored parameters, and wherein the analyzing module includes a processor for executing stored instructions to compare parameters of the energy distribution function with the stored parameters.

5. The urine detection system of claim 4, wherein the inducer and the energy-converting module are movable relative to one another.

6. The urine detection system of claim 5, wherein the inducer and the energy-converting module are tuned to conditionally resonate with one another.

7. The urine detection system of claim 6, wherein the energy-converting module is insulated from urine.

8. The urine detection system of claim 6, wherein the energy-converting module is configured to lose its ability to enterer a state of resonance when short-circuited by urine.

9. The urine detection system of claim 6, wherein the energy-converting module is configured for selective attachment to a urine collection article.

10. The urine detection system of claim 6, wherein the energy-converting module is incorporated into a urine collection article.

11. The urine detection system of claim 4, wherein the analyzing module is configured to measure an induced signal at the energy-converting module.

12. The urine detection system of claim 11, further comprising a second energy-converting module, wherein the analyzing module is configured to monitor a relative difference in the induced signals at each energy-converting module.

13. The urine detection system of claim 12, wherein the energy-converting modules are spaced in fixed positions on opposite sides of the inducer.

14. The urine detection system of claim 4, wherein the analyzing module includes a memory for storing the parameters corresponding to the known wetness conditions.

15. The urine detection system of claim 4, wherein the energy-converting module includes a mechanical converter for converting energy from the magnetic field to mechanical energy.

16. The urine detection system of claim 4, wherein two or more energy-converting modules are configured to respond differently to the same magnetic field.

17. The urine detection system of claim 4, wherein the analyzing module is configured to extract data embedded in transferred energy.

18. A urine detection system, comprising:

an inducer configured to generate a magnetic field within an effective distance of a potentially wetted area;

an energy-converting module configured to conditionally engage in mutual induction with the inducer; and an analyzing module configured to construct a magnetic energy distribution function that models an energy distribution pattern between the inducer and the energy-converting module, wherein the analyzing module is further configured to apply the magnetic energy distribution function to a set of stored parameters corresponding to known wetness conditions to identify a wetness condition of the potentially wetted area;

wherein the energy-converting module is one of a plurality of energy-converting modules, each energy-converting module configured to conditionally engage in mutual induction with the inducer.

19. The urine detection system of claim 18, wherein the plurality of energy-converting modules constitute a urine detection network for detecting relative amounts of urine at a plurality of regions of a urine collection article.

20. The urine detection system of claim 18, wherein the plurality of energy-converting modules are configured as one resonator.

21. A urine detection system, comprising:

an inducer configured to generate a magnetic field within an effective distance of a potentially wetted area;

an energy-converting module configured to conditionally engage in mutual induction with the inducer; and an analyzing module configured to construct a magnetic energy distribution function that models an energy distribution pattern between the inducer and the energy-converting module, wherein the analyzing module is further configured to apply the magnetic energy distribution function to a set of stored parameters corresponding to known wetness conditions to identify a wetness condition of the potentially wetted area;

wherein the analyzing module implements a real-time adaptive monitoring strategy to construct the energy distribution function.

22. A urine detection system, comprising:

an inducer configured to generate a magnetic field within an effective distance of a potentially wetted area;

an energy-converting module configured to conditionally engage in mutual induction with the inducer; and an analyzing module configured to construct a magnetic energy distribution function that models an energy distribution pattern between the inducer and the energy-converting module, wherein the analyzing module is further configured to apply the magnetic energy distribution function to a set of stored parameters corresponding to known wetness conditions to identify a wetness condition of the potentially wetted area;

wherein the energy-converting module includes a coil for conducting an electric current induced by the magnetic field.

23. A urine detection system, comprising:

an inducer configured to generate a magnetic field within an effective distance of a potentially wetted area;

an energy-converting module configured to conditionally engage in mutual induction with the inducer; and an analyzing module configured to construct a magnetic energy distribution function that models an energy distribution pattern between the inducer and the energy-converting module, wherein the analyzing module is further configured to apply the magnetic energy distribution function to a set of stored parameters corresponding to known wetness conditions to identify a wetness condition of the potentially wetted area;

wherein the analyzing module compares a magnetic energy distribution function constructed during an ascending frequency sweep of the magnetic field with a magnetic energy distribution function constructed during a descending frequency sweep of the magnetic field to identify a hysteretic effect.

24. A urine detection system, comprising:

an inducer configured to generate a magnetic field;

a sampling coil configured to convert magnetic energy of the magnetic field into an induced signal;

an analyzing module configured to monitor induced signal behavior at the sampling coil and recognize induced signal behavior that indicates a volume of urine is within an effective distance from the sampling coil.

25. The urine detection system of claim 24, wherein the sampling coil is fixed adjacent the inducer.

26. The urine detection system of claim 24, further comprising a reference coil configured to convert magnetic energy of the magnetic field into an induced signal, wherein the analyzing module is configured to monitor a relative difference in induced signal behavior at the sampling coil compared to the reference coil, and recognize a relative difference that indicates a volume of urine is within an effective distance from the sampling coil.

27. The urine detection system of claim 26, wherein the sampling coil and the reference coil are respectively fixed adjacent opposite sides of the inducer.

28. The urine detection system of claim 24, wherein the analyzing module implements a real-time adaptive monitoring strategy.

* * * * *